United States Patent [19]
Takayanagi

[11] Patent Number: 5,945,564
[45] Date of Patent: Aug. 31, 1999

[54] 2,2-DIDEUTERO-5-AMINOLEVULINIC ACID

[75] Inventor: Hisao Takayanagi, Kanagawa, Japan

[73] Assignee: Mitsubishi Chemical Corporation, Tokyo, Japan

[21] Appl. No.: 08/981,494

[22] PCT Filed: Jul. 12, 1996

[86] PCT No.: PCT/JP96/01948

§ 371 Date: Jan. 9, 1998

§ 102(e) Date: Jan. 9, 1998

[87] PCT Pub. No.: WO97/03042

PCT Pub. Date: Jan. 30, 1997

[30] Foreign Application Priority Data

Jul. 12, 1995 [JP] Japan ................................ 7-176254

[51] Int. Cl.$^6$ ................................................. C07C 229/08
[52] U.S. Cl. ........................... 562/567; 424/9.61; 424/9.3
[58] Field of Search .......................... 562/567; 424/9.61, 424/9.3

[56] References Cited

U.S. PATENT DOCUMENTS

| | | | |
|---|---|---|---|
| 5,042,488 | 8/1991 | Ackerman . | |
| 5,234,940 | 8/1993 | Kennedy et al. | 514/410 |
| 5,284,973 | 2/1994 | Ebata et al. | 562/567 |
| 5,380,935 | 1/1995 | Takeya et al. | 562/567 |

FOREIGN PATENT DOCUMENTS

| | | |
|---|---|---|
| 6-206883 | 7/1994 | Japan . |
| 9101727 | 2/1991 | WIPO . |
| 93/13403 | 7/1993 | WIPO . |

OTHER PUBLICATIONS

Patent Abstracts of Japan, vol. 014, No. 318 (C–0738), Jul. 9, 1990, Kajiwara Masahiro.
Patent Abstracts of Japan, vol. 018, No. 568, (C–1266), Oct. 31, 1994, Matsudaira Taeko.
Lerman et al., Journal of Organic Chemistry, vol. 46, No. 2, 1981, Easton, US, pp. 468–470, XP002073236.
Copy of the International Preliminary Examination Report in English.
Shimba et al., Chem. Pharm. Bull., vol. 38, No. 9, pp. 2610–2613 (1990).
English excerpt of Shin et al., Heisei–4 No. 03558029, p. 38 (1993).
Derwent Abstract No. WPI Acc. No. 94–275883/199434.
Behrman et al., J. Am. Chem. Soc., vol. 80, pp. 3717–3718 (1958).
Tagge et al., J. Am. Chem. Soc. vol. 118, pp. 2634–2643 (1996).
Caron et al., J. Org. Chem., vol. 50, including pp. 1556–1561 (1985).
Chini et al., Tetrahedron Letters, vol. 31, No. 39, pp. 5641–5644 (1990).
Saito et al., Tetrahedron Letters, vol. 30, No. 31, pp. 4153–4156 (1989).
Sutowardoyo et al., Tetrahedron: Asymetry, vol. 2, No. 6, pp. 437–444 (1991).
Van Hillegersberg et al., Gastroenterology, vol. 103, pp. 647–651 (1992).
Appleton et al., Bioorganic & Medical Chemistry Letters, vol. 6, No. 11, pp. 1191–1194 (1996).
Jaffe et al., Biochemistry, vol. 29, No. 36, pp. 8345–8350 (1990).
Jaffe et al., Biochemistry, vol. 27, No. 12, pp. 4475–4481 (1988).
Battersby et al., J. Chem. Soc., Chem. Commun. vol. 13, pp. 645–647 (1981).

*Primary Examiner*—Gary Geist
*Assistant Examiner*—Rosalynd Keys
*Attorney, Agent, or Firm*—Greenblum & Bernstein, P.L.C.

[57] ABSTRACT

2,2-Dideutero-5-aminolevulinic acid or its salt, or a hydrate or a solvate thereof, preferably 2,2-dideutero-5-aminolevulinic acid hydrochloride, and a process for preparing 2,2-dideutero-5-aminolevulinic acid are provided. The 2,2-Dideutero-5-aminolevulinic acid provided by the present invention is useful as a contrast medium for MRI diagnosis.

3 Claims, 1 Drawing Sheet

2,2-DIDEUTERO-5-AMINOLEVULINIC ACID

TECHNICAL FIELD

The present invention relates to 2,2-dideutero-5-aminolevulinic acid useful as a contrast medium for MRI (magnetic resonance imaging). More specifically, the present invention relates to 2,2-dideutero-5-aminolevulinic acid and its salt, and a hydrate or a solvate thereof, and to a contrast medium for MRI comprising said substance as an essential component.

BACKGROUND ART

MRI is an excellent technique which can achieve accurate diagnosis of a disease by visibly imaging morphological alterations of a living tissue from a pathological viewpoint. MRI is one of diagnostic methods which have already been utilized widely. Currently available MRI, utilizing $^1H$ as a detection nucleus, forms an image based on differences of relaxation time of $^1H$ nucleus. The differences reflect water molecules existing in distinguishable environments in a living body which depend on a sort of a tissue they exist or depend on the presence or absence of pathological abnormality of a tissue.

Distinctions of different environments and sharpness of images can be achieved by influencing the relaxation time of $^1H$ nucleus. MRI contrast media are often used for this purpose. MRI contrast media presently used are based on various kinds of concepts, however, it is common for all of the contrast media to be used for MRI diagnosis which utilizes $^1H$ nucleus as a detection nucleus. These MRI contrast media are administered intravascularly, with some exceptions of certain contrast media for gastrointestinal tract. Accordingly, an advantage of MRI diagnosis, i.e., it causes almost no pain to a patient, is spoiled. Therefore, MRI contrast media have been desired which can be orally administered and cause little pain to patients.

Another class of MRI diagnostic techniques has also been studied in which water molecules in living bodies are not measured and an NMR-spectroscopically detectable nucleus is utilized as a detection nucleus other than $^1H$. For example, $^{19}F$, $^{23}Na$, $^{31}P$, and $^{13}C$ can be used as the detection nucleuses. These techniques, utilizing a detection nucleus that does not exist in living tissues, enable an imaging which uses a detection nucleus as a tracer that is not detectable in MRI diagnosis utilizing $^1H$ as a detection nucleus. These techniques also provide information about chemical shifts which cannot be obtained by MRI diagnosis utilizing $^1H$ as a detection nucleus. Therefore, the techniques are extremely useful.

Deuterium ($D=^2H$) is a stable nucleus that can be NMR-spectroscopically detected (for example, Chem. Pharm. Bull. Vol. 38, No. 9, pp.2610–2613, 1990; and Development of superconductive type NMR system for in vivo molecules, Heisei-4, No. 03558029, p38, 1993). In addition, its natural existing ratio is quite a low level, i.e., 0.015%, which means almost no existence in living bodies. Therefore, MRI diagnosis utilizing deuterium as a detection nucleus is expected to be an extremely useful diagnostic method. Nevertheless, little study has been conducted about contrast media containing deuterium as a detection nucleus (see, for example, U.S. Pat. No. 5,042,488 and Japanese Patent Unexamined Publication No. (Hei)6-206883/1994).

Accordingly, an object of the present invention is to provide a contrast medium for MRI diagnosis which comprises deuterium as a detection nucleus. More specifically, the object is to provide a contrast medium which contains deuterium as a detection nucleus and have a high affinity to a specific tissue of a living body. Another object of the present invention is to provide a contrast medium for MRI diagnosis which has the aforementioned characteristic features and can be administered orally.

DISCLOSURE OF THE INVENTION

The inventors of the present invention conducted various researches to achieve the foregoing objects, and as a result, they found that 2,2-dideutero-5-aminolevulinic acid administered to a living body was detectable by MRI, and that the acid specifically accumulated in certain tissues in a living body, e.g., liver, thereby high contrasting effect was obtained. They also found that the above contrasting effect of 2,2-dideutero-5-aminolevulinic acid was also well achieved by oral administration. The present invention was completed on the basis of these findings.

The present invention thus provides 2,2-dideutero-5-aminolevulinic acid and its salts, and hydrates and solvates thereof. According to another aspect of the present invention, there are provided contrast media for MRI diagnosis which comprise a substance selected from the group consisting of 2,2-dideutero-5-aminolevulinic acid and its salt, and a hydrate and a solvate thereof.

According to further aspect of the present invention, there are provided a process for preparing 2,2-dideutero-5-aminolevulinic acid which comprises the steps of: (a) deuterating 5,5-dimethoxy-2-piperidone, and (b) hydrolyzing the deuterated compound obtained in the above step; and a process for preparing 2,2-dideutero-5-aminolevulinic acid which comprises the steps of: (c) epoxidating the double bond of 2,2-dideutero-4-pentenoic acid, (d) reacting the epoxy compound obtained in the above step with an azide compound to allow the ring opening of the epoxy ring, (e) oxidizing the hydroxyl group (which may optionally be protected) of the ring-opened compound obtained in the above step; and (f) reducing the azido group to convert into amino group.

Figure 1:
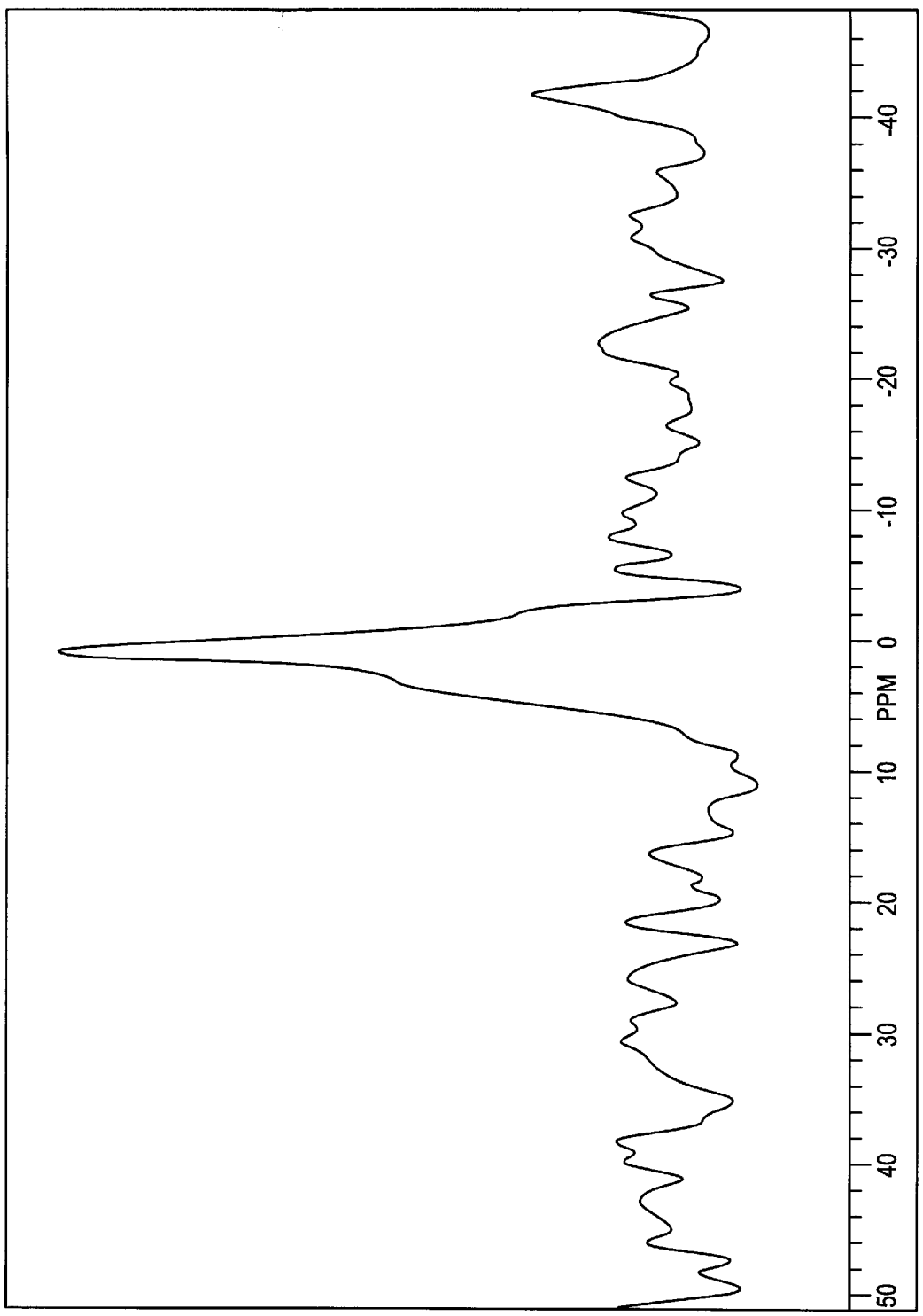
FIG. 1 is a spectrum of a contrast medium for MRI diagnosis according to the present invention when measured by MRI.

BEST MODE FOR CARRYING OUT THE INVENTION 2,2-Dideutero-5-aminolevulinic acid of the present invention is represented by the following formula (I):

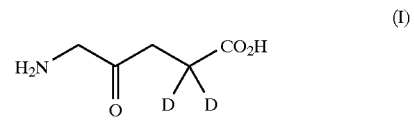

Examples of salts which can be formed with the above 2,2-dideutero-5-aminolevulinic acid include, for example, inorganic acid salts such as hydrochloride, hydrobromide, hydriodide, nitrate, and phosphate; organic acid salts such as succinate, oxalate, fumarate, maleate, lactate, tartrate, citrate, acetate, glycolate, methanesulfonate, and toluenesulfonate; alkali metal salts; alkaline earth metal salts; ammonium or alkylammonium salts and the like. The above 2,2-dideutero-5-aminolevulinic acid and salts thereof may form a hydrate or a solvate. Examples of the solvate include those formed with methanol, ethanol, isopropanol, acetone, ethyl acetate, methylene chloride and the like.

Among the compounds of the present invention, an example of the most preferred compound includes hydrochloride of 2,2-dideutero-5-aminolevulinic acid.

The compound of the present invention can be prepared, for example, according to the reaction route set out below.

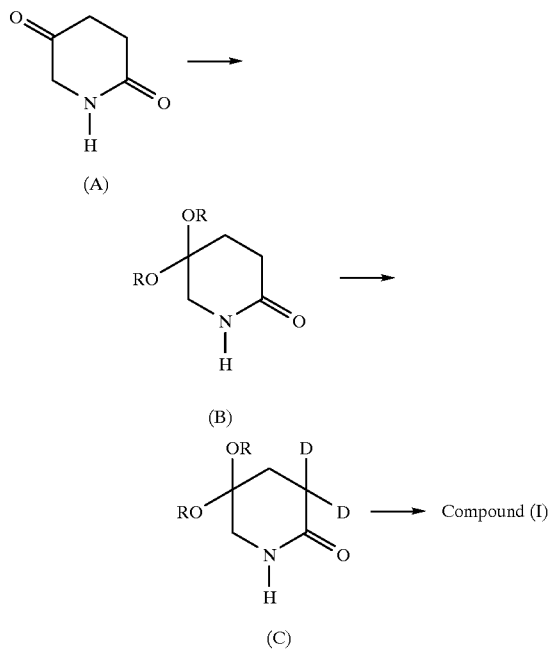

(In the above formulas, R represents a lower alkyl group such as methyl group and ethyl group.)

Piperidine-2,5-dione (A) described in a literature (J. Am. Chem. Soc., 80, 3717 (1958)) is allowed to react with a lower monoalcohol such as methanol or ethanol, or a with a diol such as ethylene glycol in the presence of an acid catalyst or dehydrating agent, and then the product is treated with an orthoester in the presence of an acid catalyst to obtain 5,5-dimethoxy-2-piperidone (B) whose carbonyl group at the 5-position is protected as an acetal. 5,5-Dimethoxy-2-piperidone (B) is subjected to hydrogen/deuterium exchange reaction using a deuterated compound in the presence of a base to obtain 3,3-dideutero-5,5-dimethoxy-2-piperidone (C), and then the resulting product is subjected to acidic hydrolysis to obtain 2,2-dideutero-5-aminolevulinic acid as a corresponding acid salt.

As the acid catalyst used in the preparation of Compound (B) from Compound (A) by the reaction with an alcohol, either of a protic acid such as hydrochloric acid, p-toluenesulfonic acid, or phosphoric acid, or an aprotic acid such as calcium chloride or boron trifluoride etherate may be used. The amount of the catalyst is generally from 1 equivalent to a catalytic amount, preferably a catalytic amount. As the dehydrating agent, calcium chloride is generally used so as to also act as a molecular sieve and an acid catalyst. The reaction is generally carried out by using the alcohol also as a solvent at a temperature of from 0° C. to a boiling point of the alcohol. The reaction may also be performed while dehydration is carried out by azeotropic distillation using a suitable solvent such as methylene chloride, ether, or toluene. As the orthoester, methyl orthoformate, ethyl orthoformate and the like may be used, and a corresponding alcohol such as methanol and ethanol can be used as a solvent. As the catalyst, acid catalysts those exemplified for the reaction with an alcohol may be used.

In the preparation of Compound (C) from Compound (B), a compound that easily dissociates deuterium such as deuterium oxide ($D_2O$) and deuterated methanol ($CH_3OD$ or $CD_3OD$) may be used as the deuterated compound. As the base, those soluble in the deuterated compound and capable of abstracting an α-proton of the ketone, and those having no dissociative proton may be used. For example, deuterated sodium hydroxide, a metal alkoxide such as sodium methoxide may be used. A deuterium content ratio of Compound (C) may be appropriately chosen depending on a deuterium content ratio and molar equivalents of a deuterated compound used in the reaction. In general, the deuterated compound may be used in an amount of from 1 to 200 equivalents so as to serve as a solvent, and the base may be used in a catalytic amount. The hydrogen/deuterium exchange reaction may be generally performed at a reaction temperature of from −20° C. to a boiling point of a solvent, preferably from 0° C. to 50° C., for 30 minutes to 10 days, preferably 5 hours to 2 days.

Examples of the acid used in the preparation of 2,2-dideutero-5-aminolevulinic acid from Compound (C) include, for example, pharmaceutically acceptable inorganic acids such as hydrochloric acid or hydrobromic acid, and organic acids such as methanesulfonic acid or p-toluenesulfonic acid. The reaction may preferably be carried out at a temperature of from 0° C. to 200° C., preferably from 50° C. to 100° C., for 30 minutes to 5 days, preferably 3 hours to 10 hours by using 0.1 to 10 equivalents, preferably 1 to 3 equivalents of the acid based on Compound (C) and by using water alone or water that contains a water-miscible organic solvent as methanol, ethanol, or tetrahydrofuran as a solvent.

Compound (I) can also be prepared from 2,2-dideutero-4-pentenoic acid (D), for example, according to the synthetic route set out below.

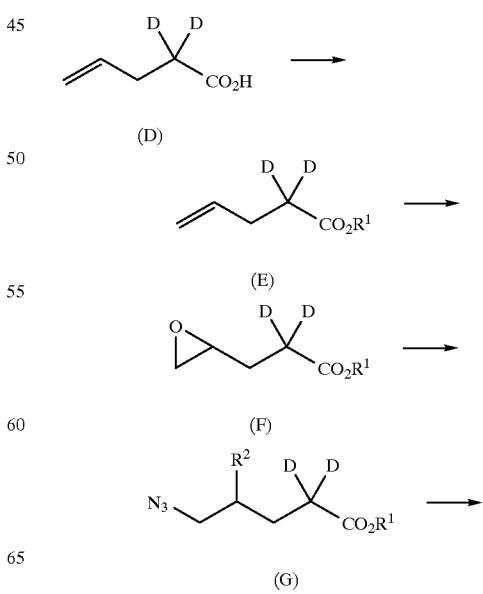

-continued

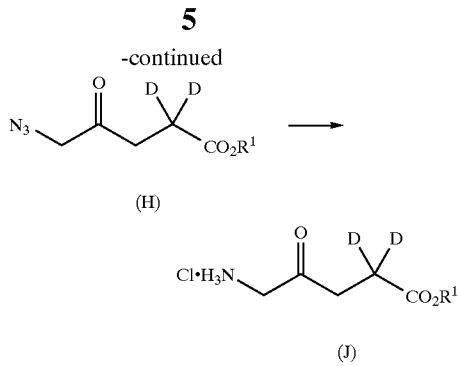

(In the formulas mentioned above, $R^1$ represents a lower alkyl group such as methyl group or ethyl group, or benzyl group, and $R^2$ represents hydroxyl group which may optionally be protected with a substituted silyl group.)

Compound (D) can be synthesized by the method described in a literature (J. Am. Chem. Soc., 118, 2634 (1996)), or the compound can also be prepared by introducing allyl group into acetic acid-$d_4$.

Compound (E) can be prepared from Compound (D) by a conventional method for esterification, for example, (1) a process comprising the step of treatment with diazomethane, (2) a process comprising the steps of conversion into an acid chloride and subsequent reaction with an alcohol, (3) a process comprising the step of dehydration with an alcohol in the presence of an acid catalyst such as mineral acids, organic acids, or Lewis acids, or (4) a process involving the use of an agent for activating carboxyl group such as dicyclohexylcarbonyldiimide, carbonyldiimidazole or the like.

Then, Compound (F) can be prepared by subjecting the above obtained compound to a method for epoxidation of an isolated double bond such as, for example, a method comprising the step of treatment with an oxidizing agent such as organic peracids, alkyl hydroperoxides, or hydrogen peroxide, a method comprising the step of treatment with an N-halocarboxylic acid amide such as N-bromosuccinimide in a water-containing organic solvent and subsequent treatment of the resulting halohydrin with a base. As the organic peracid, peracetic acid, m-chloroperbenzoic acid or the like can be used. The reaction can be performed by using 0.1 to 10 equivalents, preferably 1 to 1.5 equivalents of an organic peracid at a reaction temperature of from −20° C. to 150° C., preferably 0° C. to 100° C., for 1 hour to ten days, preferably 5 hours to 3 days, in a suitable organic solvent such as methylene chloride or chloroform. When an alkyl hydroperoxide or hydrogen peroxide is used, a metal oxide complex of, for example, titanium, aluminium, vanadium, molybdenum and the like can be used as a catalyst. By suitably choosing reaction conditions, it may be possible to prepare Compound (F) from Compound (D) without isolation or purification of Compound (E).

Compound (G) can be prepared from Compound (F), prepared by the aforementioned method, according to a method for a ring opening of an epoxy ring with azide anion, for example, a method comprising the step of reaction with ammonium azide in an alcoholic solvent (see, J. Org. Chem., 50, 1557 (1985)), a method comprising the step of reaction with sodium azide in acetonitrile in the presence of a metal salt such as lithium perchlorate (see, Tetrahedron Letters, 31, 5641 (1990)), a method comprising the step of reaction with an azide compound such as trimethylsilyl azide or tri-n-butylstannyl azide in the absence of a catalyst (see, Tetrahedron Letters, 30, 4153 (1989)), a method comprising the step of reaction with an azide compound such as trimethylsilyl azide or tri-n-butylstannyl azide in the presence of a catalyst (see, Tetrahedron: Asymmetry, 2, 437 (1991)) or the like.

In the reactions mentioned above, a compound whose hydroxyl group is protected with t-butyldimethylsilyl group can be prepared by using t-butyldimethylsilyl azide or t-butyldimethylstannyl azide, for example, instead of trimethylsilyl azide or tri-n-butylstannyl azide. In the reaction with ammonium azide, particularly when a compound wherein $R^1$ is methyl group or ethyl group is used, the ester group is sometimes susceptible to hydrolysis so as to produce a compound wherein $R^1$ is hydrogen atom, i.e., a carboxylic acid salt. In this compound, the hydrogen atom of $R^1$ may be subjected to dehydration reaction with the hydroxyl group of $R^2$ to give a lactone. Furthermore, Compound (G) wherein $R^1$ is methyl group and $R^2$ is hydroxyl group can be prepared by directly treating an extraction solution of the carboxylic acid with an esterifying agent such as diazomethane. The aforementioned lactone compound can be converted into a carboxylic acid salt by reaction with a metal hydroxide such as lithium hydroxide or sodium hydroxide, and therefore, a lactone compound formed in the above method can be converted into an ester compound wherein $R^2$ is hydroxyl group. The substituted silyl group that protects the hydroxyl group of $R^2$ can be easily removed to convert into a compound wherein $R^2$ is hydroxyl group by, for example, dissolving the protected compound in a suitable protic solvent such as methanol and stirring the solution.

By using Compound (G) wherein $R^2$ is hydroxyl group obtained by the aforementioned method, Compound (H) can be prepared according to a method for oxidizing a secondary alcohol into a ketone, for example, (1) a chromic acid oxidation using Jones' reagent, pyridinium chlorochromate or the like, (2) a dimethyl sulfoxide (DMSO) oxidation using DMSO/sulfur trioxide/pyridine mixture, DMSO/trifluoroacetic anhydride mixture or the like, (3) a hypohalogenous acid oxidation using sodium hypochlorite, calcium hypochlorite or the like. Depending on the type of the oxidizing agent, for example, where the oxidation is carried out by using Jones' reagent, Compound (H) can be prepared directly from Compound (G) having hydroxyl group protected with substituted silyl group as $R^2$ without a deblocking step.

Compound (J) can be prepared from Compound (H), obtained by the aforementioned method, by carrying out catalytic reduction using a catalyst for catalytic hydrogenation such as palladium deposited on activated carbon, palladium black, or platinum oxide in an alcohol corresponding to $R^1$ as a solvent in the presence of 1 equivalent or more of hydrochloric acid. Then, the compound of formula (I) can be obtained by subjecting Compound (J) to acid hydrolysis in an aqueous solution. Where $R^1$ is benzyl group, or when the reaction is performed in a water-containing solvent instead of an alcohol, the compound of formula (I) can be prepared without isolation of Compound (J).

The compound of formula (I) according to the present invention can be used as a contrast medium for MRI diagnosis. As the contrast medium of the present invention, the compound of formula (I), per se, may be used, or alternatively, the compound may be used as a pharmaceutical composition together with a pharmaceutically acceptable carrier. The contrast medium of the present invention can be administered orally or parenterally, and may be administered as a composition for oral administration as a formulation such as, for example, granules, fine granules, powders, tablets, hard syrups, soft capsules, syrups, emulsions, suspensions, liposomes, solutions or the like, or a composition for parenteral administration as a formulation such as injections, drip infusions, suppositories or the like. The contrast medium of the present invention is characterized in that it can achieve a sufficient contrasting effect by oral administration, however, intravenous administration as an injection is also preferable for a rapid contrasting diagnosis. Accumulation in a tissue such as hepatic tissue is a feature of the contrast medium for MRI diagnosis of the present invention, and therefore, the medium can be used as a contrast medium selective to a cancerous tissue such as hepatic cancer, arteriosclerosis, a rheumatic site and the like. Dose may generally be about 100 mg to about 10 g, preferably about 500 mg to about 5 g for oral administration.

Examples of excipients used for manufacturing solid compositions for oral administration include, for example, lactose, saccharose, starch, talc, cellulose, dextrin, kaolin, calcium carbonate and the like. Liquid compositions for oral administration including emulsions, syrups, suspensions, solutions and the like may be admixed with, for example, inert liquid mediums such as ordinarily used diluents such as vegetable oils, and in addition, they may be formulated with auxiliaries such as moistening agents, suspending aids, sweeteners, aromatics, colorants, preservatives and other. A liquid composition for oral administration may be prepared, and then the liquid composition may be encapsulated in capsules made of absorbable material such as gelatin. Examples of solvents or suspension mediums used for the preparation of compositions for parenteral administration such as injection include, for example, water, propylene glycol, polyethylene glycol, benzyl alcohol, ethyl oleate, lecithin and the like. For the preparation of the aforementioned pharmaceutical compositions, conventional methods well-known to those skilled in the art may be utilized.

EXAMPLES

The present invention will be specifically explained below by referring to Examples. However, the scope of the present invention is not limited to the following Examples. Designations of the compounds described in Examples such as Compound (A) correspond to the compound designations shown in the above schemes.

Example 1
Synthesis of Compound B (R=methyl group)

About 5 mg of p-toluenesulfonic acid was added to a solution of methyl orthoformate (5 ml), and the resulting mixture was then added to a solution of 2,5-piperidinedione (1.8 g, 16 mmol) in methanol (20 ml). The mixture was heated under reflux for 12 hours. After cooling, triethylamine (1 ml) was added to the mixture, and then the mixture was concentrated by using a rotary evaporator. The residue was purified by silica gel column chromatography ($CHCl_3$:MeOH=15:1), and then recrystallized from ethyl acetate/ether to obtain 5,5-dimethoxy-2-piperidone as the desired compound (1.85 g, 81%). m.p. 89–90° C.; $^1$H-NMR ($CDCl_3$, 300 MHz) δ: 2.01 (t, 2H, J=7.0 Hz, $NCOCH_2$—), 2.43 (t, 2H, J=7.0 Hz, $NCOCH_2CH_2$—), 3.25 (s, 6H, OMe), 3.36 (d, 2H, J=2.5 Hz, $NCH_2C(OMe)_2$), 5.89 (bs, 1H, NH). P-SIMS (Glycerin matrix) 182 ($M^+$+1.8%), 160 (100%), 128 (34%), 101 (5%).

Example 2
Synthesis of Compound (C)

5,5-Dimethoxy-2-piperidone prepared in Example 1 (500 mg, 3.4 mmol) was dissolved in deuterated methanol ($CD_3OD$, 5 ml) under nitrogen atmosphere, and then the solution was added with a 40% solution of NaOD in $D_2O$ (0.05 ml) and the mixture was stirred at room temperature overnight. After cooling, acetic acid was gradually added to the mixture to adjust its pH to about 6.5, and then the mixture was concentrated by using a rotary evaporator. The solvent was further removed by using a vacuum pump, and then the residue was added with chloroform (5 ml) and the mixture was stirred and filtered. The insoluble solids were washed with chloroform, and the filtrate was concentrated by using a rotary evaporator. The residue was recrystallized from ethyl acetate/ether to obtain 3,3-dideutero-5,5-dimethoxy-2-piperidone as the desired compound (485 mg, 95%). m.p. 87–88° C.; $^1$H-NMR ($CDCl_3$, 300 MHz, TMS) δ: 1.99 (s, 2H, $NCOCD_2CH_2$—), 3.25 (s, 6H, OMe), 3.35 (d, 2H, J=2.5 Hz, $NCH_2C(OMe)_2$), 6.93 (bs, 1H, NH). P-SIMS (Glycerin matrix) 184 ($M^+$+1.5%), 162 (100%), 130 (31%), 103 (5%).

Example 3
Synthesis of Compound (I) of the present invention 3,3-Dideutero-5,5-dimethoxy-2-piperidone prepared in Example 2 (500 mg, 3.4 mmol) was dissolved in 1N aqueous hydrochloric acid under nitrogen atmosphere, and the solution was stirred over an oil bath at 80° C. for 5 hours. After the mixture was concentrated by using a rotary evaporator, the residue was recrystallized from a mixture of ethanol and ether to obtain 2,2-dideutero-5-aminolevulinic acid hydrochloride as the desired compound (462 mg, 80%).

m.p. 147–149° C.; $^1$H-NMR ($D_2O$, 300 MHz) δ: 2.75 (s, 2H, —$CH_2CD_2$—), 3.99 (s, 2H, $NCH_2$—). P-SIMS (Glycerin matrix) 134 ($M^+$+1%), 116 (18%).

Example 4
Synthesis of Compound (D)

A solution of N-butyllithium in n-hexane (1M solution, 207 ml, 0.34 mol) was added to a solution of diisopropylamine (48 ml, 0.34 mol) in tetrahydrofuran (200 ml) at −10° C. to −7° C. with stirring. To the resulting diisopropylamide solution, acetic acid-$d_4$ (10 g, 0.156 mol) and hexamethylphosphoramide (90 ml) were added at the same temperature. After 30 minutes, allyl bromide (13.3 ml, 0.156 mol) was added to the mixture to allow the internal temperature rose from −7° C. up to 30° C. After the mixture was stirred at room temperature overnight, almost all of tetrahydrofuran was evaporated under reduced pressure. The residue was stirred over an ice bath and added with chilled 1N aqueous hydrochloric acid so as to become acidic, and then organic substances were extracted with diethyl ether. The ether layer was dried ($MgCl_2$) and concentrated, and the resulting residue was distilled to obtain 2,2-dideutero-5-pentenoic acid as the desired compound (9.3 g, 58%).

b.p. 79–82° C. (9 mmHg); $^1$H-NMR ($CDCl_3$, 300 MHz) δ: 2.39 (d, 2H, J=6.3 Hz, —$CH_2CD_2$—), 5.01–5.13 (m, 2H, $CH_2$=), 5.77–5.89 (m, 1H, $CH_2$=$CH$—).

Example 5
Synthesis of Compound (E) ($R^1$=methyl group)

A solution of the carboxylic acid obtained in Example 4 (9.1 g, 89 mmol) in methylene chloride (27 ml) was stirred on an ice-water bath, and the solution was added portionwise with carbonyldimmidazole (17.3 g, 106 mmol). After the mixture was stirred for 3 hours, methanol (5.4 ml, 133 mmol) was added to the mixture, and then stirring was further continued overnight. The reaction mixture was washed with chilled water and saturated brine, and the organic phase was dried ($MgCl_2$) and concentrated. The residue was distilled to obtain the desired methyl ester compound (3.8 g, 26%).

b.p. 126–127° C.; $^1$H-NMR (CDCl$_3$, 300 MHz) δ: 2.38 (d, 2H, J=6.0 Hz, =CHC$\underline{H}_2$), 3.68 (s, 3H, OMe), 4.98–5.09 (m, 2H, CH$_2$=), 5.77–5.89 (m, 1H, CH$_2$=C$\underline{H}$—).

Example 6
Synthesis of Compound (F)

m-Chloroperbenzoic acid (purity: 55%, 7.5 g, 24 mmol) was added portionwise to a solution of the ester compound obtained in Example 5 (2.3 g, 20 mmol) in methylene chloride (120 ml) with stirring. After stirring was continued for 24 hours at room temperature, saturated aqueous sodium hydrogen carbonate was added to the mixture on an ice bath, and then the resulting mixture was stirred vigorously. The organic phase was separated, and the aqueous phase was extracted with methylene chloride and the extract was combined with the organic layer. The resulting organic layer was washed with water and dried (MgCl$_2$). The solvent was evaporated under reduced pressure, and the resulting residue was distilled under reduced pressure to obtain the desired epoxy ester compound (2.2 g, 85%).

b.p. 98–99° C. (36 mmHg); $^1$H-NMR (CDCl$_3$, 300 MHz) δ: 1.77 (bdd, 1H, J=8.5, 4.0 Hz, C$\underline{H}_a$H$_b$CD$_2$—), 1.98 (bdd, 1H, J=8.5, 2.7 Hz, CH$_a\underline{H}_b$CD$_2$—), 2.51 (dd, 1H, J=4.9 Hz, 2.7 Hz, C$\underline{H}_a$H$_b$O—), 2.76 (t, 1H, J=2.7 Hz, CH$_a\underline{H}_b$CD$_2$—), 2.99 (m, 1H, C$\underline{H}$CH$_2$CD$_2$), 3.69 (s, 3H, OMe).

Example 7
Synthesis of Compound (F)

A methylene chloride solution containing an ester compound was obtained from the carboxylic acid obtained in Example 4 (7.5 g, 73.5 mmol) by an esterification and post-treatments in the same manner as in Example 5. The resulting solution, without distillation and purification, was oxidized with m-chloroperbenzoic acid in the same manner as in Example 6, which gave the same compound as the epoxy ester compound obtained in Example 6 (8.0 g, 82%).

Example 8
Synthesis of Compound (G)

A mixture of the epoxy ester compound obtained in Example 6 (7.5 g, 56.7 mmol), trimethylsilyl azide (12 ml, 90 mmol), and DMF (12 ml) was heated with stirring on an oil bath at 90° C. under nitrogen gas atmosphere for 40 hours. After cooling, excess reactants and DMF were evaporated under reduced pressure (about 42° C./9 mmHg), and the residue was purified by column chromatography with a small amount of silica gel (n-hexane:ethyl acetate=20:1) to obtain the desired azide compound (13.4 g, 95%).

$^1$H-NMR (CDCl$_3$, 300 MHz) δ: 0.20 (s, 9H, —SiMe$_3$), 1.85 (m, 2H, C$\underline{H}_2$CD$_2$), 3.21 (dd, 1H, J=12.5, 7.7 Hz, C$\underline{H}_a$H$_b$N$_3$), 3.28 (dd, 1H, J=12.5, 4.3 Hz, CH$_a\underline{H}_b$N$_3$), 3.72 (s, 3H, OMe), 3.86–3.93 (m, 1H, CHO—).

Example 9
Synthesis of Compound (H)

A solution of the azide compound obtained in Example 8 (13.1 g, 53 mmol) in acetone (150 ml) was stirred under ice cooling, and then the solution was added dropwise with Jones' reagent (4 [O] mmol/ml, 25 ml). After the dropwise addition was completed, the ice-water bath was removed, and then stirring was continued until the starting material was disappeared on a thin layer chromatography. Then, almost all of acetone was evaporated from the reaction mixture under reduced pressure, ether and water were added to the residue and the phases were separated. The organic phase was washed twice with water and dried (MgCl$_2$), and then concentrated under reduced pressure. The resulting residue was purified by silica gel column chromatography (n-hexane:ethyl acetate=7:2) to obtain the ketone compound (6.3 g, 69%).

$^1$H-NMR (CDCl$_3$, 300 MHz) δ: 2.73 (s, 2H, CH$_2$CD$_2$), 3.69 (s, 3H, —OMe), 4.03 (s, 2H, N$_3$CH$_2$—).

Example 10
Synthesis of Compound (J)

Concentrated hydrochloric acid (0.5 ml) was added to a solution of the azide-carbonyl compound obtained in Example 9 (440 mg, 2.5 mmol) in methanol (10 ml), and the mixture was allowed to absorb hydrogen in the presence of 10% palladium/carbon (50 mg) to perform catalytic hydrogenation at room temperature for about 2 hours. The catalyst was removed by filtration and the catalyst was washed, and then the filtrate was concentrated to obtain the desired amine hydrochloride (440 mg, 94%).

m.p. 118–121° C.; $^1$H-NMR (CDCl$_3$, 300 MHz) δ: 2.87 (s, 2H, CH$_2$CD$_2$), 3.66 (s, 3H, —OMe), 4.09 (s, 2H, NH$_2$CH$_2$—).

Example 11
Synthesis of Compound (I)

The azide-carbonyl compound obtained in Example 9 (3.9 g, 22.5 mmol) was dissolved in methanol (70 ml), and catalytic hydrogenation was performed at room temperature in the presence of concentrated hydrochloric acid (2.5 ml) and 10% palladium/carbon (400 mg) in the same manner as in Example 10. The resulting crude amine hydrochloride was dissolved in 1N aqueous hydrochloric acid (20 ml), and the solution was left stand for 24 hours at room temperature. After the completion of the reaction was confirmed by silica gel thin layer chromatography (developing solution, n-butanol:water:acetic acid=6:2.5:1.5), the reaction mixture was concentrated to obtain crude crystals. The crystals were recrystallized from a mixture of methanol and ethyl ether to give 2,2-dideutero-5-aminolevulinic acid hydrochloride having the same physicochemical properties as those of the compound (I) obtained in Example 3 (3.54 g, 92%).

The 2,2-dideutero-5-aminolevulinic acid (hydrochloride) of the present invention thus prepared was in the form of colorless or pale yellow crystals. In the $^1$H-NMR spectrum, the proton at the 2-position observed in non-deuterated 5-aminolevulinic acid (2.59 ppm; t, 2H, J=2.5 Hz) was not observed, and the proton at the 3-position (2.77 ppm, t, 2H, J=2.5 Hz) was observed as singlet at 2.75 ppm. The results verified that the protons at the 2-position of 5-aminolevulinic acid were substituted with deuterium atoms. In addition, the SI-MS spectrum of the 2,2-dideutero-5-aminolevulinic acid hydrochloride gave a molecular ion peak corresponding to the molecular weight larger by 2 compared to the measuring value of 5-aminolevulinic acid hydrochloride, which also supported the structure of 2,2-dideutero-5-aminolevulinic acid. A 0.1 M aqueous solution of the 2,2-dideutero-5-aminolevulinic acid (hydrochloride) obtained in Example 3 was left to stand at room temperature for one month and then concentrated, and the residue was subjected to $^1$H-NMR spectrum analysis. As a result, no decrease of the D atoms was observed.

Test Example 1

A 0.1 M aqueous solution (D atom concentration: 200 μM) of a compound of the present invention (the compound of Example 3) filled in a 10 ml-glass sample bottle was subjected to MRI measurement by using an MR apparatus BEM400/80 (SMIM Co., Ltd., 2 Tesla) under the conditions of: spectrum range: 10 KHz; FOV=25 cm; slice thickness= 10 mm; TR=0.3 second; TE=50 m-second; sampling number: 256; imaging matrix: 256×256 points; and integration number: 64 times. The measurement gave a clear D-image.

The result suggests that D atoms contained in an organic compound other than deuterium oxide ($D_2O$) can also achieve MR imaging.

Mice as experimental animals (balb/c, 5-week old, female, 16–17 g) were inoculated with colon carcinoma (colon 26) by subcutaneous administration at their outer femoral region in the amount of $5 \times 10^6$ cells per mouse, and the compound of the present invention was administered to the mice by forced oral administration (2000 mg/kg, 0.1 ml/10 g of body weight) on the 13th day (cancer volume: about 1 $cm^3$), and the mice was sacrificed with pentobarbital six hours after the administration.

These animals were subjected to MR analysis by using the same MR apparatus as described above. Resonance frequencies of $^1H$ and D were 85.562 and 13.134 MHz, respectively. Measuring conditions were as follows: spectrum range: 5000 Hz; repetition time (TR): 0.41 second; waiting time: 200 $\mu$second; and integration: 2048. As a result, the D spectrum shown in FIG. 1 was obtained.

It is known that 5-aminolevulinic acid is converted into porphyrin in living body after administration to an animal, and accumulates in cancerous, arteriosclerotic, and rheumatic tissues. According to an animal test using rats, the amount of accumulation as porphyrin in a cancerous tissue reached to 20–40 $\mu$mol of porphyrin per 1 g of cancerous tissue (see, Gastroenterology, 103, 647–651 (1992)). Porphyrin consists of eight molecules of 5-aminolevulinic acid. The compounds of the present invention is featured in that two hydrogen atoms not eliminated in the porphyrin biosynthesis pathway are substituted with D atoms, and accordingly, if 20 $\mu$mol/g tissue of porphyrin accumulates in a cancerous tissue, the amount of D atom in the cancerous tissue is calculated as $20 \times 8 \times 2 = 320$ $\mu$mol/g tissue, which corresponds to the concentration of 320 $\mu$M. D spectrums were practically observable by using tumor-bearing animals, and the results indicate that a selective D-imaging of cancerous, arteriosclerotic, rheumatic tissue and other can be achieved by using the contrast medium for MRI diagnosis of the present invention.

Industrial Applicability

The compounds of the present invention are useful as contrast media for MRI diagnosis utilizing deuterium ($D = {}^2H$) as a detection nucleus. In particular, since the compounds of the present invention are orally absorbable, they are useful as contrast media for MRI diagnosis which do not spoil the advantage of MRI, i.e., almost no pain to a patient.

What is claimed is:

1. A process for preparing 2,2-dideutero-5-aminolevulinie acid which comprises:
   (a) deuterating 5,5-dimethoxy-2-piperidone; and
   (b) hydrolyzing a deuterated compound obtained in (a).
2. A process for preparing 2,2-dideutero-5-aminolevulinic acid which comprises:
   (a) epoxidating the double bond of 2,2-dideutero-4-pentenoic acid to obtain an epoxy compound;
   (b) reacting the epoxy compound obtained in (a) with an azide compound to allow ring-opening of the epoxy ring to obtain a ring-opened compound;
   (c) oxidizing an hydroxyl group of the ring-opened compound obtained in (b); and
   (d) reducing the azido group for conversion into amino group.
3. The process according to claim 2, wherein the hydroxyl group is a protected hydroxyl group.

* * * * *